US011696936B2

(12) United States Patent
Costantini

(10) Patent No.: US 11,696,936 B2
(45) Date of Patent: Jul. 11, 2023

(54) TREATMENT OF CANCER

(71) Applicant: OSE IMMUNOTHERAPEUTICS, Nantes (FR)

(72) Inventor: Dominique Costantini, Paris (FR)

(73) Assignee: OSE IMMUNOTHERAPEUTICS, Nantes (FR)

( * ) Notice: Subject to any disclaimer, the term of this patent is extended or adjusted under 35 U.S.C. 154(b) by 116 days.

(21) Appl. No.: 16/767,144

(22) PCT Filed: Nov. 27, 2017

(86) PCT No.: PCT/EP2017/080543
§ 371 (c)(1),
(2) Date: May 27, 2020

(87) PCT Pub. No.: WO2019/101347
PCT Pub. Date: May 31, 2019

(65) Prior Publication Data
US 2020/0384067 A1 Dec. 10, 2020

(51) Int. Cl.
*A61K 38/10* (2006.01)
*A61K 38/08* (2019.01)
*A61P 35/00* (2006.01)
*A61K 45/06* (2006.01)

(52) U.S. Cl.
CPC .............. *A61K 38/10* (2013.01); *A61K 38/08* (2013.01); *A61P 35/00* (2018.01); *A61K 45/06* (2013.01)

(58) Field of Classification Search
CPC ........ A61K 38/03; A61K 38/10; A61K 38/08; A61K 39/0011; A61P 35/00
See application file for complete search history.

(56) References Cited

U.S. PATENT DOCUMENTS

2018/0169200 A1  6/2018  Costantini

FOREIGN PATENT DOCUMENTS

| WO | WO 2017/000983 | 1/2017 |
| WO | WO 2017/173321 | 10/2017 |

OTHER PUBLICATIONS

ClinicalTrials.gov, "Glossary of Common Site Terms", https://clinicaltrials.gov/ct2/about-studies/glossary; accessed on May 6, 2022; 20 pages (Year: 2022).*
Ellis et al. "Immune Checkpoint Inhibitors for Patients With Advanced Non-Small-Cell Lung Cancer: A Systematic Review", Clinical Lung Cancer, pp. 444-459; Sep. 2017 (Year: 2017).*
Barve et al. "Induction of Immune Responses and Clinical Efficacy in a Phase II Trial of IDM-2101, a 10-Epitope Cytotoxic T-Lymphocyte Vaccine, in Metastatic Non-Small-Cell Lung Cancer", Journal of Clinical Oncology, 2008, pp. 4418-4425 (Year: 2008).*
History of Changes for Study: NCT02654587 Study of OSE2101 Versus Standard Treatment as 2nd or 3rd Line in HLA-A2 Positive Patients With Advanced NSCLC. Version 1, First posted Jan. 13, 2016. pp 1-6 (Year: 2016).*
Efficiency, (n.d.) Farlex Partner Medical Dictionary. (2012). Retrieved Dec. 1, 2022 from https://medical-dictionary.thefreedictionary.com/efficiency (Year: 2012).*
ClinicalTrials.gov, Identifier: NCT02654587, "Study of OSE2101 Versus Standard Treatment as 2nd or 3rd Line in HLA-A2 Positive Patients With Advanced NSCLC After Failure of Immune Checkpoint lnhibitor(ATALANTE 1)", First posted Jan. 13, 2016 (Year: 2016).*
Dammeijer, F et al. "Rationally combining immunotherapies to improve efficacy of immune checkpoint blockade in solid tumors" *Cytokine & Growth Factor Reviews*, 2017, pp. 5-15, vol. 36.
Buchbinder, E. I. et al. "CTLA-4 and PD-1 Pathways; Similarities, Differences, and Implications of Their Inhibition" *American Journal of Clinical Oncology*, Feb. 2016, pp. 98-106, vol. 39, No. 1.
Anonymous: "A Randomized Parallel Group Phase III Trial of OSE 2101 as 2nd Line After Prior Platinum-based Chemotherapy Failure or as 3rd Line After Platinum-failure and Checkpoint Inhibitor-failure Compared With Standard Treatment (Docetaxel or Pemetrexed) in HLA-A2 Positive Patients With Locally Advanced (IIIB) Unsuitable for Radiotherapy or Metastatic Non-Small-Cell Lung Cancer" *ClinicalTrials*, Jan. 12, 2016, pp. 1-9, XP-002783122, Protocol ID: OSE2101C301, retrieved from the Internet on Jul. 17, 2818: URL:https://clinicaltrials.gov/ct2/history/NCT02654587?V 1=View#StudyPageTop.
Written Opinion in International Application No. PCT/EP2017/080543, dated Aug. 8, 2018, pp. 1-8.
History of Changes for Study NCT02654587, "Study of OSE2101 Versus Standard Treatment as 2nd or 3rd Line in HLA-A2 Positive Patients With Advanced NSCLC (ATALANTE1)", last update posted Aug. 15, 2017, retrieved from ClinicalTrials.gov on Apr. 14, 2022.
History of Changes for Study NCT02654587, "Study of OSE2101 Versus Standard Treatment as 2nd or 3rd Line in HLA-A2 Positive Patients With Advanced NSCLC After Failure of Immune Checkpoint Inhibitor (ATALANTE1)", last update posted Jun. 28, 2018, retrieved from ClinicalTrials.gov on Apr. 14, 2022.

* cited by examiner

*Primary Examiner* — Lianko G Garyu
(74) *Attorney, Agent, or Firm* — Saliwanchik, Lloyd & Eisenschenk

(57) ABSTRACT

The present invention relates to improved treatment of cancer, in particular to a treatment with a composition of CTL peptides for patients after a treatment with an immune checkpoint inhibitor.

17 Claims, No Drawings
Specification includes a Sequence Listing.

SEQUENCE LISTING

```
<160> NUMBER OF SEQ ID NOS: 11

<210> SEQ ID NO 1
<211> LENGTH: 9
<212> TYPE: PRT
<213> ORGANISM: Artificial Sequence
<220> FEATURE:
<223> OTHER INFORMATION: synthetic peptide

<400> SEQUENCE: 1

Arg Leu Leu Gln Glu Thr Glu Leu Val
1               5

<210> SEQ ID NO 2
<211> LENGTH: 10
<212> TYPE: PRT
<213> ORGANISM: Artificial Sequence
<220> FEATURE:
```

```
<223> OTHER INFORMATION: synthetic peptide

<400> SEQUENCE: 2

Tyr Leu Gln Leu Val Phe Gly Ile Glu Val
1               5                   10

<210> SEQ ID NO 3
<211> LENGTH: 9
<212> TYPE: PRT
<213> ORGANISM: Artificial Sequence
<220> FEATURE:
<223> OTHER INFORMATION: synthetic peptide

<400> SEQUENCE: 3

Leu Leu Thr Phe Trp Asn Pro Pro Val
1               5

<210> SEQ ID NO 4
<211> LENGTH: 9
<212> TYPE: PRT
<213> ORGANISM: Artificial Sequence
<220> FEATURE:
<223> OTHER INFORMATION: synthetic peptide

<400> SEQUENCE: 4

Lys Val Phe Gly Ser Leu Ala Phe Val
1               5

<210> SEQ ID NO 5
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: xaa is alpha-aminobutyric acid

<400> SEQUENCE: 5

Lys Leu Xaa Pro Val Gln Leu Trp Val
1               5

<210> SEQ ID NO 6
<211> LENGTH: 9
<212> TYPE: PRT
<213> ORGANISM: Artificial Sequence
<220> FEATURE:
<223> OTHER INFORMATION: synthetic peptide

<400> SEQUENCE: 6

Ser Met Pro Pro Pro Gly Thr Arg Val
1               5

<210> SEQ ID NO 7
<211> LENGTH: 9
<212> TYPE: PRT
<213> ORGANISM: Artificial Sequence
<220> FEATURE:
<223> OTHER INFORMATION: synthetic peptide

<400> SEQUENCE: 7

Ile Met Ile Gly His Leu Val Gly Val
1               5

<210> SEQ ID NO 8
<211> LENGTH: 9
```

```
<212> TYPE: PRT
<213> ORGANISM: Artificial Sequence
<220> FEATURE:
<223> OTHER INFORMATION: synthetic peptide

<400> SEQUENCE: 8

Lys Val Ala Glu Ile Val His Phe Leu
1               5

<210> SEQ ID NO 9
<211> LENGTH: 9
<212> TYPE: PRT
<213> ORGANISM: Artificial Sequence
<220> FEATURE:
<223> OTHER INFORMATION: synthetic peptide

<400> SEQUENCE: 9

Tyr Leu Ser Gly Ala Asp Leu Asn Leu
1               5

<210> SEQ ID NO 10
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is d-alanine
<220> FEATURE:
<221> NAME/KEY: MISC_FEATURE
<222> LOCATION: (3)..(3)
<223> OTHER INFORMATION: Xaa is a cyclohexylalanine
<220> FEATURE:
<221> NAME/KEY: MISC_FEATURE
<222> LOCATION: (13)..(13)
<223> OTHER INFORMATION: Xaa is d-alanine

<400> SEQUENCE: 10

Xaa Lys Xaa Val Ala Ala Trp Thr Leu Lys Ala Ala Xaa
1               5                   10

<210> SEQ ID NO 11
<211> LENGTH: 9
<212> TYPE: PRT
<213> ORGANISM: Artificial Sequence
<220> FEATURE:
<223> OTHER INFORMATION: synthetic peptide

<400> SEQUENCE: 11

Ala Leu Leu Glu Ile Ala Ser Cys Leu
1               5
```

TREATMENT OF CANCER

CROSS-REFERENCE TO RELATED APPLICATION

This application is the U.S. national stage application of International Patent Application No. PCT/EP2017/080543, filed Nov. 27, 2017.

The Sequence Listing for this application is labeled "Seq-List.txt" which was created on May 4, 2020 and is 3 KB. The entire content of the sequence listing is incorporated herein by reference in its entirety.

FIELD OF THE INVENTION

The present invention relates to the field of medicine, in particular of oncology, and more particularly the present invention relates to the treatment of cancer.

BACKGROUND OF THE INVENTION

ICI are Becoming Standard of Care in Various Cancer Types:

The immune checkpoint inhibitors (ICI or CKI) targeting cytotoxic T-lymphocyte-associated protein 4 (CTLA-4 e.g., ipilimumab tremelimumab), programmed cell death-1 (PD-1 e.g., nivolumab pembrolizumab), and PD-1 ligand (PD-L1 e.g., atezolizumab, durvalumab, avelumab) are now widely applied in clinical cancer treatments and are registered as standard therapy in various advanced or metastatic cancers (FDA historical approvals of ICI). These approved indications are today including melanoma, NSCLC (non-small cell lung cancer), urothelial cancers, renal cancers, head and neck cancers, Hodgkin's lymphoma, gastric and esophageal cancers, colorectal cancers subtypes, hepatocellular carcinoma, metastatic Merkel cell carcinoma. These ICI indications could be after failure of first line (when the first treatment doesn't work as chemotherapy used in first line) or directly indicated in first line related to the expression of a ICI biomarker or not. Other cancers are also explored clinically with the ICI class, as breast cancers, ovarian cancer, glioblastoma. CTLA-4 and PD-1 are brakes expressed on the surface of effector T cells blocking T cell responses, suppressing their activation and effector functions. Immunotherapies ICI that block these brakes (CTLA-4, PD-1, and PD-L1) can restore and augment cytotoxic T-cell responses, leading to potentially resilient responses and prolonged overall survival (OS) with tolerable toxicity profile.

ICI Established as First Line or Second Line Treatment:

ICI are used alone in first line when PD-L1 ligand is overexpressed (FDA approval of pembrolizumab) or in combination with chemotherapy in first line (e.g., pembrolizumab other conditional approval by FDA in first line to be used with pemetrexed and carboplatin for patients with previously untreated advanced non squamous NSCLC, regardless of whether their tumors express the protein PD-L1 (Langer C. J. et al, Lancet Oncol. 2016, 17(11):1497-1508) demonstrating superiority of the combination versus chemotherapy used in first line treatment.

ICI are also used after radiotherapy or chemo-radiotherapy (as maintenance of first line results) or after first line failure of chemotherapy (second line).

Comparators used in Clinical ICI Trials are Different Considering First or Second Lines Options:

Nivolumab studied after chemotherapy or chemoradiotherapy (i.e. Scott J. A. et al, 2016, N Engl J Med; 377: 1919-1929) is demonstrating superiority versus placebo in such specific maintenance or duration of the stabilization of the cancer after chemoradiation with decrease of progression time in less invasive cancer. Clinical ICI trials demonstrating efficacy in second line on advanced or locally advanced cancers (after first line of a specific standard chemotherapy defined by cancer type) are compared to another chemotherapy used as standard treatment in second line, establishing superiority on overall survival versus a second line chemotherapy (Brahmer J et al, N Engl J Med. 2015; 373(2):123-35).

ICI Trials are Including a lot of Combination Trials:

The aim of combination is to demonstrate superiority versus ICI alone or versus the comparator used in the combination as standard of care of a specific cancer. ICI are used in various combination with other therapeutic strategies (antiangiogenic compounds, various chemotherapies, targeted therapy and other ICI).

Combination with other ICI acting on different T cell targets are also demonstrating efficacy versus monotherapy as anti-CTLA4 plus anti PD-1 (Larkin Jet al; N Engl J Med 2015; 373:23-34). Other ICI clinical combination are radiotherapy, chemoradiotherapy.

Some other immune checkpoint molecules, including lymphocyte-activation gene 3 (LAG-3), T-cell immunoglobulin mucin-3 (TIM-3), and V-domain immunoglobulin suppressor of T-cell activation (VISTA), are also clinically explored alone or in combination with anti PD-L1/anti PD-1/anti-CTLA4. Despite promising studies, combination therapies of immune-checkpoint blockade with other different immune checkpoints have so far slightly enhanced the clinical efficacy, while amplifying adverse effects.

ICI Combination with Cancer Vaccines:

In this specific cancer vaccines/ICI combinations, the objective is to promote antigen release and presentation in parallel with ICI action. Cancer vaccine further amplifies T cell activation, that inhibits trafficking of regulatory T cells or MSDCs, that stimulates intratumoral T cell infiltration, that increases cancer recognition by T cells, and that stimulates tumor killing. The combination of ICI with peptides (gp100, MART-1, NY-ESO-1) demonstrates immunologic activity with promising survival in high-risk resected melanoma, justifying further study (Gibney G T, et al. Clin Cancer Res, 2015, 21(4):712-20).

A vaccine with a live-attenuated Listeria strain encoding the human papillomavirus (HPV) 16 oncoprotein E7 (ADXS11-001) in combination with anti-PD-L1 (durvalumab) is studied in a phase I/II trial in patients with cervical cancer or HPV-positive head and neck cancer Furthermore, a live-attenuated Listeria strain encoding for prostate-specific antigen level (PSA) (ADXS31-142) in combination with anti-PD-1 (pembrolizumab) is studied in a phase I/II trial in patients with prostate cancer. Various combination approaches with immune-checkpoint blockade have been studied in preclinical models and clinical studies, the number of clinical trials studying such ICI/cancer vaccines combination field is huge. To date the clinical efficacy and toxicity data are still limited.

Therapeutic Strategy after ICI Failure:

There is still a clear need for new therapies after failure of ICI as there is no rescue therapy identified up to now after ICI.

Despite the initial success of ICI-treatment, still a minority of patients experiences responses. Primary and secondary resistance to immune checkpoint blockade therapy precludes patients from achieving durable responses and long-term survival.

A plethora of mechanisms underlie ICI resistance ranging from low immunogenicity, "hyper-exhausted" T-cell not able to respond to ICI, inadequate generation or recruitment of tumor-specific T cells, immunosuppression by Myeloid suppressive cells, tumor associated macrophages (TAMs) or Treg, local suppression by stromal cells (cancer associated fibroblasts -CAF-, endothelial cells) to acquired genetic alterations leading to immune escape (Dammeijer F. et al; 2017, Cytokine & Growth Factor Reviews 36, 5-15). The treatment response heterogeneity of ICI may reflect the ability of tumors to adapt to immune pressure through the loss of antigenicity and immunogenicity as well as through their ability to establish an immunosuppressive microenvironment (Beatty G. L. et al; Immune Escape Mechanisms as a Guide for Cancer Immunotherapy 2015, Clinical Cancer Research).

Primary resistance can result from the absence of a functional immune response to a poorly immunogenic tumor with low neo-antigen expression, low mutational load, dendritic cells not capable of antigen trafficking and presentation, low recruitment of tumor-specific T cells and immune inhibition by inhibitory immune cell populations in the Tumor Micro-Environment TME.

Secondary resistance is related to continuous therapeutic pressure may result in the development of acquired resistance. Mechanisms include upregulation of other co-inhibitory molecules and loss of tumor (neo)antigen expression.

In the literature related to Tumor vaccines, publications are focused only on how this class could synergize with direct combination with checkpoint blockade. In the meta-analysis of Dammejier, they assessed the efficacy of tumor vaccination in lung cancer (NSCLC) with implications for studies investigating combination immunotherapy in NSCLC (Dammeijer F et al, J Clin Oncol. 2016; 34(26): 3204-12).

Today oncologists could propose salvage therapy beyond ICI failure using chemotherapy after progression trying to see tumor responses (Szabados B. et al, Eur Urol. 2017 Sep. 13, S0302-2838).

Recently, the picture regarding treatment of advanced NSCLC has completely changed with 3 immune checkpoint inhibitors (ICI) being approved for second line therapy after platinum combination failure, and one of them for first line. Several combinations are also under investigation. The reference therapy for second line is now ICI, demonstrating superiority versus chemotherapy.

However, there is still a clear and important medical need for new therapies after failure of ICI as there is no rescue therapy identified up to now after ICI. Then, new therapies after failure of ICI are clearly needed.

SUMMARY OF THE INVENTION

The present invention relates to the treatment with a composition of CTL peptides of HLA A2 positive patients after failure of a treatment with an immune checkpoint inhibitor, whatever the previous response to immune checkpoint inhibitor. Indeed, the inventors surprisingly observed that the patients treated with the composition of CTL peptides after failure of a treatment with an immune checkpoint inhibitor experience a better therapeutic response, e.g. lower occurrence of death, than the patients not previously treated with immune checkpoint inhibitor. In addition, the inventors observed a better response to a further treatment with an immune checkpoint inhibitor after a progression following the treatment of the peptide composition.

Therefore, the present invention relates to a peptide composition for use in the treatment of a cancer of an HLA-A2 (Human Leukocyte Antigen A2) positive patient,
wherein the patient received an immune checkpoint inhibitor as last treatment, alone or in combination with another cancer therapy; and
wherein the peptide composition comprises the peptide aKXVAAWTLKAAa (SEQ ID No 10, with X and a respectively indicating cyclohexylalanine and d-alanine) and at least 4, 5, 6, 7, 8 or 9 peptides selected from the group consisting of RLLQETELV (SEQ ID No 1), YLQLVFGIEV (SEQ ID No 2), LLTFWNPPV (SEQ ID No 3), KVFGSLAFV (SEQ ID No 4), KLBPVQLWV (SEQ ID No 5, with B indicating α-aminoisobutyric acid), SMPPPGTRV (SEQ ID No 6), IMIGHLVGV (SEQ ID No 7), KVAEIVHFL (SEQ ID No 8), and YLSGADLNL (SEQ ID No 9).

Preferably, the peptide composition comprises the following peptides aKXVAAWTLKAAa (SEQ ID No 10, with X and a respectively indicating cyclohexylalanine and d-alanine), RLLQETELV (SEQ ID No 1), YLQLVFGIEV (SEQ ID No 2), LLTFWNPPV (SEQ ID No 3), KVFGSLAFV (SEQ ID No 4), KLBPVQLWV (SEQ ID No 5, with B indicating α-aminoisobutyric acid), SMPPPGTRV (SEQ ID No 6), IMIGHLVGV (SEQ ID No 7), KVAEIVHFL (SEQ ID No 8), and YLSGADLNL (SEQ ID No 9).

The cancer can be a cancer selected from the group consisting of NSCLC (non-small cell lung cancer) and small cell lung cancer, melanoma, urothelial cancer, mesothelioma, breast cancers, primary brain cancers such as glioblastoma, ovarian, uterine carcinoma, especially uterine corpus and/or uterine cervix carcinoma, head and neck cancer, colorectal cancers, gastric and esophageal cancers, renal cancers, hepatocellular carcinoma, sarcoma, germ cell tumors, leukemia, lymphoma such as Hodgkin's lymphoma, skin cancers such as Merkel cell carcinoma, testicular cancers and bladder cancers, preferably NSCLC, melanoma, urothelial cancer, renal cancer, head and neck cancer, colorectal cancer, pancreatic cancer, gastric and esophageal cancers, breast cancer, ovarian cancer, brain cancer and lymphoma, and more preferably NSCLC.

Preferably, the patient has an advanced cancer, preferably with metastasis, for instance at stage III, including stage IIIA, IIIB, Mc, or IV, preferably stage IIIB, IIIc or IV.

The patient can be either a responder or not to the immune checkpoint inhibitor of the last treatment.

In one aspect, the patient received one or several lines of treatment prior to the administration by the peptide composition, preferably one, two, three or four lines of treatment, more preferably one, two, or three lines of treatment, in particular one or two lines of treatment.

For instance, the peptide composition is to be administered every one-four weeks, preferably every two-three weeks, more preferably every 3 weeks. Optionally, the peptide composition is to be administered at least twice, preferably at least three times.

Preferably, the peptide composition is to be administered in a period of one week to three months after cancer progression with the last treatment with the immune checkpoint inhibitor, alone or in combination with another cancer therapy, preferably a period of two week to two months.

The present invention also relates to an immune checkpoint inhibitor for use in the treatment of a cancer of a patient as defined above, wherein the patient has a cancer progression after administration of the peptide composition.

The present invention further relates to a peptide composition as defined above and an immune checkpoint inhibitor with sequential administration for use in the treatment of a cancer of a HLA-A2 positive patient,
   wherein the patient received an immune checkpoint inhibitor as last treatment, alone or in combination with another cancer therapy,
   wherein the peptide composition is to be administered after the last treatment with the immune checkpoint inhibitor;
   wherein the immune checkpoint inhibitor is to be administered when a cancer progression occurs with the treatment with the peptide composition;
   optionally wherein the peptide composition is to be further administered when a cancer progression occurs with the treatment with the immune checkpoint inhibitor and the immune checkpoint inhibitor is to be further administered when a cancer progression occurs with the treatment with the peptide composition.

The immune checkpoint inhibitor can be a CTLA-4 inhibitor and/or a PD-1 or PD-L1 inhibitor; IDO inhibitors (Indoleamine-pyrrole 2,3-dioxygenase i.e., indoximod). For instance, the immune checkpoint inhibitor can be selected in the group consisting of pembrolizumab, nivolumab, BMS936559, MEDI4736, AMP-224, AMP-514, MEDI0680, MPDL328OA, avelumab, atezolizumab, durvalumab, tremelimumab and ipilimumab.

DETAILED DESCRIPTION OF THE INVENTION

In a first aspect, the present invention relates to a peptide composition as defined herein for use in the treatment of a cancer of an HLA-A2 (Human Leukocyte Antigen A2) positive patient, wherein the patient received an immune checkpoint inhibitor as last treatment, alone or in combination with another cancer therapy. It also relates to the use of a peptide composition as defined herein for the manufacture of a drug for the treatment of a cancer of an HLA-A2 (Human Leukocyte Antigen A2) positive patient, wherein the patient received an immune checkpoint inhibitor as last treatment, alone or in combination with another cancer therapy. It further relates to a method for treating a cancer of an HLA-A2 (Human Leukocyte Antigen A2) positive patient, wherein the patient received an immune checkpoint inhibitor as last treatment, alone or in combination with another cancer therapy, the method comprising administering a therapeutically effective amount of a peptide composition as defined herein.

In a second and additional aspect, the present invention relates to an immune checkpoint inhibitor for use in the treatment of a cancer of a patient as defined above, wherein the patient has a cancer progression after administration of the peptide composition as defined herein. The present invention also relates to the use of an immune checkpoint inhibitor for the manufacture of a drug for the treatment of a cancer of an HLA-A2 (Human Leukocyte Antigen A2) positive patient, wherein the patient has a cancer progression after administration of the peptide composition as defined herein. The present invention relates to a method for treating a cancer of an HLA-A2 (Human Leukocyte Antigen A2) positive patient, wherein the patient received an immune checkpoint inhibitor as last treatment, alone or in combination with another cancer therapy, and subsequently a peptide composition, and the patient has a cancer progression after administration of the peptide composition, the method comprising administering a therapeutically effective amount of an immune checkpoint inhibitor.

This patient received a treatment with the peptide composition after a progression or a failure with a previous treatment with an immune checkpoint inhibitor. Then, after a period of time, the patient may have a cancer progression. Then the treatment with the peptide composition is stopped and this patient is treated with an immune checkpoint inhibitor. The inventors demonstrated that this patient has a better therapeutic response to the immune checkpoint inhibitor. The immune checkpoint inhibitor can be the same or can be different from the immune checkpoint inhibitor used in the previous treatment.

In a third and additional aspect, the present invention relates to a peptide composition as defined above and an immune checkpoint inhibitor with sequential administration for use in the treatment of a cancer of a HLA-A2 positive patient,
   wherein the patient received an immune checkpoint inhibitor as last treatment, alone or in combination with another cancer therapy;
   wherein the peptide composition is to be administered after the last treatment with the immune checkpoint inhibitor;
   wherein the immune checkpoint inhibitor is to be administered when a cancer progression occurs with the treatment with the peptide composition;
   optionally wherein the peptide composition is to be further administered when a cancer progression occurs with the treatment with the immune checkpoint inhibitor and the immune checkpoint inhibitor is to be further administered when a cancer progression occurs with the treatment with the peptide composition.

The present invention also relates to a method of treatment of an HLA-A2 (Human Leukocyte Antigen A2) positive patient, wherein the patient received an immune checkpoint inhibitor as last treatment, alone or in combination with another cancer therapy, the method comprising
   a) administering a therapeutically effective amount of a peptide composition as defined herein;
   b) administering a therapeutically effective amount of an immune checkpoint inhibitor when a cancer progression occurs with the treatment with the peptide composition; and
   c) optionally administering a therapeutically effective amount of a peptide composition as defined herein;
   wherein steps a), b) and c) are sequential and wherein steps b) and c) can be repeated as long as the patient has a therapeutic benefit of the sequential treatment.

Definitions

An "epitope" is the collective features of a molecule, such as primary, secondary and tertiary peptide structure, and charge, that together form a site recognized by an immunoglobulin, T cell receptor or HLA molecule. Alternatively, an epitope can be defined as a set of amino acid residues which is involved in recognition by a particular immunoglobulin, or in the context of T cells, those residues necessary for recognition by T cell receptor proteins and/or Major Histocompatibility Complex (MHC) receptors. Epitopes are present in nature, and can be isolated, purified or otherwise prepared or derived by humans. For example, epitopes can be prepared by isolation from a natural source, or they can be synthesized in accordance with standard protocols in the art. Throughout this disclosure, epitopes may be referred in some cases as peptides or peptide epitopes.

"Human Leukocyte Antigen" or "HLA" is a human class I or class II Major Histocompatibility Complex (MHC)

protein (see, e.g., Stites, et al., IMMUNOLOGY, 8TH ED., Lange Publishing, Los Altos, Calif. (1994). HLA molecules are grouped on the basis of shared peptide-binding specificities. For example, HLA-A2 is a particular type of HLA molecules which share similar binding affinity for peptides bearing certain amino acid motifs. The methods for determining the HLA-A2 status in a patient are well-known and easy to obtain (i.e.; serological samples) by the one skilled in the art.

A "peptide epitope" is a peptide that comprises an allele-specific motif or supermotif such that the peptide will bind an HLA molecule and induce a CTL and/or HTL response. Thus, peptide epitopes of the invention are capable of binding to an appropriate HLA-A2 molecule and thereafter inducing a cytotoxic T lymphocyte (CTL) response, or a helper T lymphocyte (HTL) response, to the peptide.

A "PanDR peptide" or "PADRE®" peptide is a member of a family of molecules that binds more than one HLA class II molecule. The pattern that defines the PADRE® family of molecules can be referred to as an HLA Class II supermotif. A PADRE® molecule binds to HLA class II molecules and stimulates in vitro and in vivo human HTL responses. PADRE peptides are described in the patent EP735893.

A "CTL and/or an HTL response" is a protective or therapeutic immune response to an antigen derived from a pathogenic antigen (e.g., an antigen from an infectious agent or a tumor antigen), which in some way prevents or at least partially arrests disease symptoms, side effects or progression. The immune response may also include an antibody response which has been facilitated by the stimulation of helper T cells.

"Therapeutic line" refers to a treatment of a disease. Several therapeutic lines can be established. For instance, a first therapeutic line can be a combination of radiotherapy with chemotherapy or a chemotherapy alone, associated or not with surgery, i.e., tumor resection. The first therapeutic line can alternatively called induction therapy, primary therapy, and primary treatment. If the first therapeutic line doesn't cure the disease or it causes severe side effects, other treatment may be added or used instead. Then a second therapeutic line can comprise for instance an immune checkpoint inhibitor, alone or in combination another cancer therapy.

"Progression" refers to the situation in which the cancer progresses, for instance metastasis occurrence, new metastasis occurrence, or tumor growth.

"Responder" refers to a patient who has a therapeutic benefit with the treatment. "Non-responder" refers to a patient who has no therapeutic benefit with the treatment. The patient has a resistance (i.e. a primary resistance) to the treatment.

The Peptide Composition

The peptide composition of the invention is able to help the immune system to develop immune memory that can have long-lasting, tumor-specific effects.

An effective peptide T specific cancer immunotherapy requires induction of a wide breadth of CTL specificities. This can be best achieved with optimized epitopes targeting multiple Tumor Associated Antigens (TAAs) as a multi-epitopes combination targeting at least 5 tumor antigens and based on epitopes combination. Preferably, the at least 5 tumor antigens include or are selected among HER2/neu, CEA, MAGE2, MAGES and p53.

The peptide composition comprises a combination of epitopes that can be wild-type epitopes and modified epitopes (heteroclitic and fixed anchors epitopes). Preferably, the peptide composition comprises at least 5 epitopes.

In a preferred embodiment, the peptide composition comprises at least 5 epitopes chosen among those disclosed in Table 6 of the US application US2014/01474790 (incorporated herein by reference). More preferably, the peptide composition comprises at least 5 epitopes allowing to target the combination of the following 5 tumor antigens: HER2/neu, CEA, MAGE2, MAGE3 and p53. For instance, peptide composition may comprise at least 5, 6, 7, 8 or 9 epitopes chosen among those disclosed in Table 6 of the US application US2014/0147490.

The original combination used here (OSE-2101) is made by wild-type epitopes and modified epitopes (heteroclitic and fixed anchors epitopes). More detailed information on heteroclitic and fixed anchors epitopes can be found for instance in the patent EP1620456.

OSE-2101 is a multi-epitope T specific cancer immunotherapy composed of 10 synthetic peptides. Nine of the peptides have been designed to induce a CTL response against TAAs. More particularly, the peptide composition of the invention is designed for administration to patients for the induction of CTL directed against carcinoembryonic antigen (CEA), p53, human epidermal receptor-2/neurological (HER-2/neu) and melanoma antigen 2 and 3 (MAGE-2/3). These TAAs have been chosen based on epidemiology because they are frequently over-expressed in various advanced cancers as colon cancers, ovarian cancers, breast cancers and NSCLC. Each CTL epitope is restricted by HLA-A2 superfamily of major histocompatibility complex class I molecules, thereby providing coverage of approximately 45% of the general population. The tenth synthetic peptide is the pan-DR epitope (PADRE), a rationally designed helper T-lymphocyte (HTL) epitope included only to increase the magnitude of CTL responses.

The peptide composition of the invention, in particular the OSE-2101 composition, comprises or consists of the following peptides:

RLLQETELV  SEQ ID No 1

YLQLVFGIEV  SEQ ID No 2

LLTFWNPPV  SEQ ID No 3

KVFGSLAFV  SEQ ID No 4

KLBPVQLWV,  SEQ ID No 5 with B indicating α-aminoisobutyric acid

SMPPPGTRV  SEQ ID No 6

IMIGHLVGV  SEQ ID No 7

KVAEIVHFL  SEQ ID No 8

YLSGADLNL  SEQ ID No 9 aKXVAAWTLKAAa,  SEQ ID No 10 with X and a respectively indicating cyclohexylalanine and d-alanine.

Therefore, the peptide composition of the invention comprises the peptide aKXVAAWTLKAAa (SEQ ID No 10, with X and a respectively indicating cyclohexylalanine and d-alanine) and at least 4, 5, 6, 7, 8 or 9 peptides selected from the group consisting of RLLQETELV (SEQ ID No 1), YLQLVFGIEV (SEQ ID No 2), LLTFWNPPV (SEQ ID No 3), KVFGSLAFV (SEQ ID No 4), KLBPVQLWV (SEQ ID No 5, with B indicating α-aminoisobutyric acid), SMPPPGTRV (SEQ ID No 6), IMIGHLVGV (SEQ ID No 7), KVAEIVHFL (SEQ ID No 8), and YLSGADLNL (SEQ ID No 9).

The peptides can be synthesized using standard Boc or Fmoc chemistry for solid phase peptide synthesis starting with the appropriate resin, and purified by standard methods. Alternatively, the peptide may be produced by genetic engineering with recombinant cells or by RNA, for instance by in vitro translation system.

The peptide composition of the invention may comprise a pharmaceutically acceptable carrier or excipient. More preferably, the pharmaceutically acceptable carrier is an aqueous carrier, especially a buffer. In particular, it may comprise one or several adjuvants. For instance, adjuvants can be incomplete Freund's adjuvant, mineral oil adjuvant, aluminum hydroxide, or alum, GM-CSF. Other suitable adjuvants are well-known in the art.

In one embodiment, the peptide composition of the invention may comprise peptide pulsed antigen presenting cells, such as dendritic cells.

Preferably, in the peptide composition of the invention, the peptides are emulsified in incomplete Freund's adjuvant or the like. In a preferred embodiment, the adjuvant is a mineral oil adjuvant, similar to Incomplete Freund's Adjuvant, manufactured and supplied by Seppic SA, Paris, FRANCE. In a most preferred embodiment, the adjuvant is Montanide® ISA 51.

Each peptide of the composition can be present at a concentration of 0.1 mg/ml to 1 mg/ml, preferably 0.5 mg/ml. Preferably, all the peptides are present in the composition at the same concentration.

Preferably, the peptide composition of the invention is a sterile, preservative-free emulsion of the 10 peptides at a concentration of 0.5 mg/ml each, formulated in Montanide® ISA 51 adjuvant at a ratio of 1:1 (w:w) and filled into rubber-stoppered glass vials, and refrigerated at 2° to 8° C.

OSE-2101 is manufactured under aseptic conditions. Peptides are dissolved in three different solvents, sterile filtered, pooled and then emulsified in adjuvant via homogenization under controlled conditions. Product release testing included appearance, endotoxin, sterility, viscosity, particle size, peptide concentration of each peptide, volume, pH and potency. Preparation of OSE-2101 composition is detailed in WO2004/094454, FIG. 3A and pages 105-106, the disclosure of which being incorporated herein by reference.

Optionally, in addition to the 10 peptides of OSE-2101, the peptide composition of the present invention may further comprise additional peptides, in particular peptide epitopes used for inducing of cytotoxic T-lymphocyte (CTL) responses and targeting TAAs. For instance, the peptide composition of the present invention may further comprise a peptide as disclosed in WO2009/143843 (the disclosure of which being incorporated herein by reference), and more particularly IDO5 (SEQ ID No 11).

Previous Lines of Treatment

In particular, the patient received in the last therapeutic line an immune checkpoint inhibitor. The immune checkpoint inhibitor has been administered alone or in combination with another drug, in particular another cancer therapy.

Then, the patient had a cancer progression. The cancer progression can be either due to a failure to respond to this treatment (a primary resistance) or to a loss of therapeutic efficiency (a secondary resistance).

In a particular aspect, the last treatment includes an immune checkpoint inhibitor or a combination of an immune checkpoint inhibitor and another cancer therapy.

The cancer therapy in combination with the immune checkpoint inhibitor can be a chemotherapy, especially a platinum-based chemotherapy such as carboplatin, or a combination with a targeted therapy, a combination with another immune checkpoint inhibitor or a combination of immune checkpoint inhibitor with or after a chemo-radiotherapy.

The patient received one or several lines of treatment prior to the administration by the peptide composition, preferably one, two, three or four lines of treatment, more preferably one, two, or three lines of treatment, in particular one or two lines of treatment. In particular, the patient may have received other therapeutic line(s) before the last treatment with the immune checkpoint inhibitor. In a preferred embodiment, this/these previous therapeutic line(s) do(es) not comprise any immune checkpoint inhibitor. For instance, this/these previous therapeutic line(s) may include a chemotherapy, alone or in combination with radiotherapy and/or surgery.

The chemotherapeutic agent can be a DNA damaging antitumoral agent such as an inhibitor of topoisomerases I or II, a DNA crosslinker, a DNA alkylating agent, an antimetabolic agent and inhibitors of the mitotic spindles. For instance, the chemotherapy can be selected among cisplatin, carboplatin, cyclophosphamide, etoposide, teniposide, mitomycin, irinotecan, vinorelbine, etoposide, ifosfamide, temozolomide, fluorouracil (5FU), docetaxel, pemetrexed, navelbine.

Targeted therapy refers to therapy targeting VEGF, tyrosine kinase such as EGFR or ALK, for instance drugs that target tumor blood vessel growth (VEGF) such as bevacizumab, ramucirumab; nindetamid, tyrosine kinase inhibitors targeting EGFR such as gefitinib, erlotinib, afatinib; ALK inhibitors such as crizotinib; ceritinib and any combination thereof; MEK inhibitors such as trametinib; BRAF inhibitors such as dabrafenib; PIK3CA inhibitors; CDK4, 6 inhibitors; Aurora kinase inhibitors; PI3K/mTOR-inhibitors; PI3Kalpha inhibitors. The administration of the peptide composition as defined herein is performed after the end of the treatment with the immune check point inhibitor. There is no overlap between the two treatments. They are sequential. Preferably, the peptide composition is to be administered in a period of one week to three months after cancer progression with the last treatment with the immune checkpoint inhibitor, preferably a period of two week to two months. Preferably, the peptide composition is to be administered in a period of one week to three months after the end of the last treatment with the immune checkpoint inhibitor, preferably a period of two week to two months.

Cancer

According to a preferred aspect of the present invention, the patient has a cancer, preferably selected from the group consisting of lung cancer such as NSCLC (non-small cell lung cancer) and small cell lung cancer, melanoma, urothelial cancer, mesothelioma, breast cancers, primary brain cancers such as glioblastoma, ovarian, uterine carcinoma, especially uterine corpus and/or uterine cervix carcinoma, head and neck cancer, colorectal cancers, gastric and esophageal cancers, renal cancers, hepatocellular carcinoma, sarcoma, germ cell tumors, leukemia, lymphoma such as Hodgkin's lymphoma, skin cancers such as Merkel cell carcinoma, testicular cancers and bladder cancers, pancreatic cancer, preferably NSCLC, melanoma, urothelial cancer, renal cancer, head and neck cancer, colorectal cancer, gastric and esophageal cancers, breast cancer, ovarian cancer, brain cancer and lymphoma, pancreatic cancer and more preferably NSCLC.

In another preferred embodiment, the patient has advanced cancer. The term "advanced cancer" refers to a cancer at an advanced stage of development, i.e. a cancer invasive with no possibility of surgery or cancer that has spread in the body (metastasis). For instance, the patient has a cancer in stage III, including stage IIIA, IIIB, IIIc or IV, preferably stage IIIB, IIIc or IV.

Administration Regimen of the Peptide Composition:

For instance, the peptide composition is to be administered every one-four weeks, preferably every two-three weeks, more preferably every 3 weeks.

Optionally, the peptide composition is to be administered at least one, at least twice, or at least three times.

The administration regimen of the peptide composition comprises a priming period and optionally a boosting period.

The term "priming period" refers to the period of the vaccination process during which a central memory T cell response is induced against one or several peptides of the therapeutic peptide T specific immunotherapy.

The term "boosting period" refers to the period of the vaccination process following the priming period during which the same therapeutic peptide T specific immunotherapy is administered and the T memory immune response is sustained or enhanced.

According to a preferred aspect of the present invention, the priming period of a subject under treatment with therapeutic peptide T specific immunotherapy consists in one to three administrations of the therapeutic peptide T specific immunotherapy or vaccine.

In an even more preferred embodiment, the priming period consists in three administrations of the therapeutic peptide T specific immunotherapy or vaccine.

During this priming period, the peptide composition is administered at least once and up to seven or eight times every one-four weeks, preferably every two-three weeks, more preferably every 3 weeks, still more preferably from twice to six times every two-three weeks.

During the optional boosting period, which follows the priming period, one or several administrations of the peptide composition are realized. During this boosting period, the administration of the peptide composition occurs every two-eight months, preferably every two-three months, for instance every two month through one or two years from the beginning of the treatment with the peptide composition and then every three months.

In an alternative embodiment, the priming period is not followed by a boosting period.

The priming period and the boosting period can be separated by a rest period which does not include any administration of the peptide composition. This rest period can last four to twelve weeks.

The treatment with the peptide composition continues as long as the state of the patient is stable, namely that there is no progression in the disease. In particular, no progression means that there is no growth in the tumor and/or no spread in the cancer, i.e., metastasis.

The Immune Checkpoint Inhibitor

The immune checkpoint inhibitor can be a CTLA-4 inhibitor and/or a PD-1 or PD-L1 inhibitor; IDO inhibitors (Indoleamine-pyrrole 2,3-dioxygenase).

Several PD-1/PD-L1 inhibitors are already available or under clinical development. For instance, the PD-1/PD-L1 inhibitors can be chosen among the non-exhaustive list including pembrolizumab (Merk), nivolumab (Bristol Myers Squibb), BMS936559 an anti-PD-L1 (Bristol Myers Squibb), MEDI4736 or durvalumab (Astra Zeneca), AMP-224 Anti-PD-1 fusion protein (Astra Zeneca), AMP-514 or MEDI0680 an anti-PD-1 (Astra Zeneca), MPDL328OA atezolizumab an anti-PD-L1 (Roche), avelumab (also known as MSB0010718C from Merck KgA Serono/Pfizer). For instance, the PD-1/PD-L1 inhibitors can be chosen among those disclosed in WO2013/079174.

For instance, the CTLA-4 inhibitors can be chosen among the non-exhaustive list including tremelimumab (Medimmune/Astra Zeneca) and ipilimumab (BMS).

Accordingly, the immune checkpoint inhibitor is selected in the group consisting of pembrolizumab, nivolumab, BMS936559, MEDI4736, AMP-224, AMP-514, MPDL328OA, atezolizumab, avelumab, durvalumab, Tremelimumab and ipilimumab.

Dosage

Within the context of the invention, the term "treatment" or "treating" denotes curative, symptomatic, and preventive treatment. Pharmaceutical compositions and preparations of the invention can be used in humans with existing cancer or tumor, preferably at late stages of progression of the cancer. The pharmaceutical compositions and preparations of the invention will not necessarily cure the patient who has the cancer but will delay or slow the progression or prevent further progression of the disease, ameliorating thereby the patient's condition. In particular, the pharmaceutical compositions and preparations of the invention reduce the development of tumors, and/or prevent metastasis occurrence or development and cancer relapse. In treating the cancer, the pharmaceutical composition of the invention is administered in a therapeutically effective amount.

By "effective amount" it is meant the quantity of the pharmaceutical composition of the invention which prevents, removes or reduces the deleterious effects of brain metastases. It is understood that the administered dose may be adapted by those skilled in the art according to the patient, the pathology, the mode of administration, etc. The dosage and regimen depends on the stage and severity of the disease to be treated, the weight and general state of health of the patient and the judgment of the prescribing physician. More particularly, by "therapeutically efficient amount of the peptide composition" is intended the amount which is sufficient to increase the overall survival of a patient.

Previous cancer trials have tested escalating doses of peptide, ranging from 0.1 to 10 mg of peptide per injection dose, emulsified in incomplete Freund's adjuvant. At all doses tested, the peptide/incomplete Freund's adjuvant treatment was deemed to be safe and well tolerated, with no severe dose-related systemic toxicities being reported.

The peptide composition of the invention can be administered by any appropriate route, in particular by parenteral route such as subcutaneous, intradermal or intramuscular route or by aerosol, transmucosal, intrapleural, or intrathecal routes. In a most preferred embodiment, the peptide composition is administered subcutaneously. Preferably, the peptide composition is designed for subcutaneous injection.

Preferably, the doses of each peptide are ranging from 0.1 to 10 mg of peptide per injection dose. In a preferred embodiment, the total peptide dose for each injection or administration will be 5.0 mg (1 mL of drug product containing 0.5 mg of each peptide).

EXAMPLES

Efficacy of T Cell Neoepitopes Cocktail (OSE2101) Administered after Checkpoint Inhibitors Failure in Advanced Cancers A randomized parallel group phase III trial of OSE2101 as mainly 2nd or 3rd line compared with standard treatment (docetaxel or pemetrexed) in HLA-A2 positive patients with locally advanced (IIIB) unsuitable for radiotherapy or metastatic (IV) Non-Small-Cell Lung Cancer has been carried out. (OSE2101C301)

Primary Objective

The objective of the clinical trial was to demonstrate that OSE2101 (Arm A) is superior to standard chemotherapy used in second line, pemetrexed or docetaxel (Arm B), in prolonging overall survival (OS) in HLA-A2 positive patients with locally advanced (IIIB) or metastatic (IV) NSCLC as 2nd or 3rd line therapy after failure of prior platinum-based chemotherapy or after failure of checkpoint-inhibitor regimens used alone or in combination with platinum or radio-chemotherapy or checkpoint inhibitor failure after radio-chemotherapy checkpoint used as maintenance treatment:

The total study duration for an individual subject depends on the survival of the subject, randomization time is the baseline for OS (overall survival) calculations.

Clinical Trial

Treatments:

OSE2101 (Arm A);

OSE-2101 peptide composition consists of the following peptides:

|  | SEQ ID No 1 |
|---|---|
| RLLQETELV | |
| YLQLVFGIEV | SEQ ID No 2 |
| LLTFWNPPV | SEQ ID No 3 |
| KVFGSLAFV | SEQ ID No 4 |
| KLBPVQLWV, | SEQ ID No 5 | with B indicating α-aminoisobutyric acid

|  | SEQ ID No 6 |
|---|---|
| SMPPPGTRV | |
| IMIGHLVGV | SEQ ID No 7 |
| KVAEIVHFL | SEQ ID No 8 |
| YLSGADLNL | SEQ ID No 9 |
| aKXVAAWTLKAAa, | SEQ ID No 10 | with X and a respectively indicating cyclohexylalanine and d-alanine.

OSE2101 was administered as a 1 mL-subcutaneous injection on Day 1 every three weeks for six cycles, then every two months for the remainder of year one and finally every three months until the end of the trial. OSE2101 dose was 5 mg of peptide (0.5 mg for each peptide).

Docetaxel or Pemetrexed (Arm B).

Docetaxel or pemetrexed was administered every 3 weeks.

Docetaxel was administered at 75 mg/m² by intravenous infusion over 1 hour on Day 1 of a 21-day cycle.

Pemetrexed was administered at 500 mg/m² by intravenous infusion over 10 minutes on Day 1 of a 21-day cycle.

Treatment cycles were repeated until disease progression (RECIST) as determined by the investigator, unacceptable toxicity, or consent withdrawal. In this case the investigator was free to propose to the patient a rescue therapy (following the Best investigator choice) or a salvage therapy including a new chemotherapy, an immune checkpoint inhibitor or no treatment proposal depending on the acceptance/status of the patients.

End of treatment: 4 weeks after the last treatment administration to obtain assessments from the 4 previous weeks or 6 weeks for tumor assessments.

Follow up: every 2 months after discontinuation of treatment for the post-treatment survival status.

Inclusion Criteria

Cancer Diagnosis and Treatment

1-Histologically or cytologically proven diagnosis of lung cancer (NSCLC) that was locally advanced (stage IIIB) unsuitable for radiotherapy or metastatic (stage IV) according to the 7th edition of tumor, node, metastasis (TNM) in Lung Cancer published by the International Union Against Cancer and the American Joint Committee on Cancer.

2—Subjects with disease recurrence or progression
  a. Patients must have had progressive disease after only one prior chemotherapy regimen:
    i. It includes patients who have received one prior platinum-based chemotherapy in the adjuvant setting following surgical resection for early disease and whose disease has recurred within 12 months of completion of prior chemotherapy
    ii. It includes patients who received one prior platinum-based chemotherapy in combination with radiation therapy for Stage III locoregional disease and whose disease has recurred within 12 months of completion of prior chemotherapy
    iii. It includes patients who received 2 prior platinum-based chemotherapy regimens, if the first regimen was given as adjuvant therapy or was given in combination with radiation therapy for locally advanced disease
  or Patients have had progressive disease after therapy with an immune checkpoint inhibitor and platinum-based chemotherapy (either 1$^{st}$ line chemotherapy followed by 2$_{nd}$ line checkpoint inhibitor used alone, or 1$^{st}$ line combination of checkpoint inhibitor and chemotherapy or checkpoint inhibitor failure after radio-chemotherapy (checkpoint used as maintenance treatment) 3—Subjects with measurable or non-measurable lesions.

4—Subjects must express HLA-A2 phenotype as assessed serologically.

5—Subjects must be considered suitable for chemotherapy with either single-agent pemetrexed or docetaxel.

6—Subjects with brain metastases are eligible if treated (whole brain radiotherapy, stereotaxic radiotherapy, surgery) and have no symptoms (except for signs and symptoms related to central nervous system therapy) for at least 2 weeks before initiation of allocated treatment and are not taking any forbidden medications.

7—Any prior chemotherapy, immunotherapy, radiation therapy or surgeries must have been completed at least 3 weeks prior to initiation of study medication.

8—Any toxicity from prior therapy must have recovered to ≤Grade 1 (except alopecia). ECOG performance status 0-1 and adequate organ function were also required.

Exclusion Criteria
Cancer Diagnosis and Treatment

1. Small-cell lung cancer/mixed NSCLC with small cell component or other neuroendocrine lung cancers (typical and atypical carcinoids, large-cell neuroendocrine carcinomas). Large-cell carcinoma.

2. NSCLC that is predominantly squamous cell carcinoma, and patient had docetaxel as part of his prior chemotherapy.

3. Current or previous treatment with investigational therapy in another therapeutic clinical trial interrupted less than 4 weeks before study treatment initiation.

4. Patients whose tumor harbors EGFR gene mutation that sensitizes tumors to TKI (EGFR exon 18-21) or ALK rearrangement.

5. Ongoing immunotherapy (checkpoint inhibition, antigen immunotherapy).

6. Spinal cord compression (unless treated with the patient attaining good pain control and stable or recovered neurologic function), carcinomatous meningitis, or leptomeningeal disease.

7. Patients with squamous cell histology or non-squamous cell histology previously treated by pemetrexed and with a contraindication for docetaxel with grade ≥2 neuropathy or hypersensitivity reaction to medications formulated with polysorbate 80) as they could be randomly assigned to Arm B.

Medical History and Clinical Status

Patients with a condition requiring systemic treatment with either corticosteroids or other immunosuppressive medications, patients with immunodeficiency disease or viral infections HIV active B or C hepatitis.

Patients were randomly assigned in a 1/1 ratio. The study was randomized with strata predefined but not be blinded as study treatment and reference therapies have different routes of administration, need concomitant therapy that would not be allowed for OSE2101 (steroids) and safety profile would easily help to recognize treatment allocated. Thus, the study was open-labelled (not blind).

Randomization was stratified by
 histology (squamous vs. non-squamous),
 initial response to first line treatment (objective response: complete or partial response, vs. no objective response: stabilization or progressive disease), and
 previous treatment with immune checkpoint inhibitors ICI (yes vs. no).

Results

The study began in Q1 2016 in 9 countries and was recruiting patients with advanced and metastatic NSCLC entering in progression after chemotherapy or after checkpoint inhibitors failure. In June 2017, the clinical trial was placed on temporary pause of patient accrual following recommendation of the Independent Data Monitoring Committee (IDMC) due to an emerging risk/benefit balance of the experimental treatment.

131 subjects were entering in the trial with disease recurrence or progression after chemotherapy or after Checkpoint inhibitors. The precise information on deaths events related to arms A and B was requested unblinded by agencies (competent regulatory authorities) and these deaths event percentage results are presented below.

Population of Patients
 Arm A OSE2101: 65 patients
 Arm B Chemotherapy (pemetrexed or docetaxel depending on histology status): 66 patients There was no severe imbalance in the distribution across strata between the 2 treatment arms except for the strata NS-NO-NP, NS-O-NP.

| Strata    | Arm A (n = 65) | Arm B (n = 66) |
|-----------|----------------|----------------|
| NS-NO-NP  | 20             | 26             |
| NS-NO-P   | 5              | 7              |
| NS-O-NP   | 20             | 13             |
| NS-O-P    | 8              | 7              |
| S-NO-NP   | 4              | 3              |
| S-NO-P    | 0              | 0              |
| S-O-NP    | 3              | 4              |
| S-O-P     | 5              | 6              |

Histology: NS: Non-squamous, S: Squamous

Initial response to first line treatment NO: No objective response (stabilization or progressive disease), O: objective response (complete or partial response)

Previous treatment with immune checkpoint inhibitors NP: No previous treatment with CKI (post prior platinum-based chemotherapy), P: previous treatment with CKI whatever the number of previous lines of treatments before the last immune checkpoint inhibitor.

Comparability

The two groups were globally comparable at randomization (age, sexes, smoker status, inclusion and exclusion factors, stage of NSCLC IIIb locally invasive patients and stage IV metastatic).

Number of Previous Therapeutic Lines Before the Entry in Arm A or B:

The number of previous therapeutic lines was balanced.

| Number of patients | A | B | Total |
|---|---|---|---|
| Entry in the clinical trial for 2nd line after CKI in the 1st line of treatment | 2<br>3.08 | 5<br>7.58 | 7 |
| Entry in the clinical trial for 3rd line after CKI in the 2nd line of treatment | 14<br>21.54 | 15<br>22.73 | 29 |
| Entry in the clinical trial for 4th line after CKI in the 3rd line of treatment | 2<br>3.08 | 0<br>0.00 | 2 |
| no previous CKI before entry in the clinical trial | 47<br>72.31 | 46<br>69.70 | 93 |
| Total | 65 | 66 | 131 |

Patients entering post checkpoint failure for the $3^{rd}$ line have received nivolumab in second line of treatment. Patients entering in 2nd line have received atezolizumab plus chemotherapy in first line or durvalumab plus radiochemotherapy in maintenance or nivolumab plus chemotherapy in first line. Patients entering in $4^{th}$ line have received nivolumab in $3^{rd}$ line.

Survival Results

The results on the principal item are presented by group A or B with the number of death events allowing to define a percentage of deaths events. A Kaplan Meier curve analysis comparing the survival curves is planned only at the end of the trial.

Global review of death events by the 2 main strata post chemotherapy (no previous CKI treatment) and post checkpoint inhibitor (previous CKI treatment): A: 31/65 B: 29/66

| | | |
|---|---|---|
| No previous CKI treatment | A: 28/47 | 59.5% |
| | B: 20/46 | 44.4% |
| Previous CKI treatment | A: 3/18 | 16.6% |
| | B: 9/20* | 45% |

In patients with no previous CKI treatment (receiving chemotherapy before treatment A or B), the group A presents an unbalanced number of death events.

In the strata post checkpoint inhibitors, despite the unbalanced number of previous treatments received before checkpoint inhibitors in arm A and B, the study shows a strong and unexpected difference in favor of the group A as only 16.6% of the population is dead (83.4% is still alive) in this group (3 deaths event/18) versus 50% of the population dead in the group B receiving chemotherapy 9/18 (*2 patients withdrawn before randomization).

More specifically, for the patient entering in the clinical trial for the $3^{rd}$ line of treatment, the results are the followings.

| $3^{rd}$ line |
|---|
| A: 1/14 |
| B: 8/15* |

These first results are then confirmed in the subgroup of patients entering in $3^{rd}$ line after CKI (CKI administered in second line) as 7% of this population is dead (93% still alive) in the group A (1 death event/14) and only 43% still alive (57% of this population is dead) in the group B with 8 death events/14 (*one patient withdrawn before randomization).

Efficacy Data Observed in Arm A Independent to Previous Response to CKI

Response to previous CKI treatment is categorized as Yes (CR-PR-SD) vs No (PD).

| Subgroup | Death Events |
|---|---|
| Previous response to CKI treatment | A: 3/18 |
| | B: 9/20 |
| Yes (CR-PR-SD) | A: 2/6 |
| | B: 5/9 |
| No (PD) | A: 1/12 |
| | B: 4/11 |

Whatever the initial response on CKI treatment, patients on arm A showed a better survival than patients on arm B. This survival effect is more marked in patients without response on CKI treatment.

The peptide composition OSE2101 is able to revigorate immune system after CKI failure even for patients responding to CKI treatment and progressing (secondary resistance) or for patients not responding to CKI treatment (primary resistance).

Immunological Treatment Arm A Before CKI Treatment used as Rescue: Impact on Death Events Compared with Chemotherapy Arm?

When patients were progressing under treatment A or B, the protocol allowed to propose rescue treatments following the investigator choice (majority of patients post chemotherapy). When a CKI treatment was proposed after progression in group A or B, the initial treatment with the peptide composition OSE2101 followed by a CKI treatment decreases the number of death events when compared to the chemotherapy followed by a CKI treatment.

Death events in patients having received CKI treatment after a treatment according to either arm A or B
A: 5/18; 27.8%
B: 18/35; 51.4%

Accordingly, the number of death events for patients receiving a Checkpoint inhibitor after a treatment with the peptide composition OSE2101 is less important in arm A, in comparison to those of arm B.

Safety-Severe Adverse Events and Deaths Events

All the death events in arm A were related to progression. In arm B it was also death events by progressive disease, except for two serious adverse events (one neutropenia and one stroke event).

The serious adverse events related to OSE2101 in arm A were not different form the serious adverse event previously described and globally less severe than chemotherapy arm.

This element is important for risk benefit assessment especially after CKI treatment when the therapeutic options are very limited.

The invention claimed is:

1. A method of treating cancer in a Human Leukocyte Antigen A2 (HLA-A2) positive patient comprising administering, to a HLA-A2 positive patient having already been treated as a last treatment with an immune checkpoint inhibitor alone or in combination with another cancer therapy and has cancer progression after the last treatment, a peptide composition comprising aKXVAAWTLKAAa (SEQ ID NO: 10, with X and a, respectively, indicating cyclohexylalanine and d-alanine) and at least 4, 5, 6, 7, 8 or 9 peptides selected from the group consisting of RLLQETELV (SEQ ID NO: 1), YLQLVFGIEV (SEQ ID NO: 2), LLTFWNPPV (SEQ ID NO: 3), KVFGSLAFV (SEQ ID NO: 4), KLBPVQLWV (SEQ ID NO: 5, with B indicating α-aminoisobutyric acid), SMPPPGTRV (SEQ ID NO: 6), IMIGHLVGV (SEQ ID NO: 7), KVAEIVHFL (SEQ ID NO: 8), and YLSGADLNL (SEQ ID NO: 9) wherein the patient has a secondary resistance against the immune checkpoint inhibitor and wherein the secondary resistance is a loss of therapeutic efficiency after 3 months of treatment with the immune checkpoint inhibitor.

2. The method according to claim 1, wherein the peptide composition comprises the following peptides: aKXVAAW-TLKAAa (SEQ ID NO: 10, with X and a respectively indicating cyclohexylalanine and d-alanine), RLLQETELV (SEQ ID NO: 1), YLQLVFGIEV (SEQ ID NO: 2), LLTFWNPPV (SEQ ID NO: 3), KVFGSLAFV (SEQ ID NO: 4), KLBPVQLWV (SEQ ID NO: 5, with B indicating α-aminoisobutyric acid), SMPPPGTRV (SEQ ID NO: 6), IMIGHLVGV (SEQ ID NO: 7), KVAEIVHFL (SEQ ID NO: 8), and YLSGADLNL (SEQ ID NO: 9).

3. The method according to claim 1, wherein the cancer is a cancer selected from the group consisting of NSCLC (non-small cell lung cancer), small cell lung cancer, melanoma, urothelial cancer, mesothelioma, breast cancers, primary brain cancers, glioblastoma, ovarian cancer, uterine carcinoma, uterine corpus and/or uterine cervix carcinoma, head and neck cancer, colorectal cancers, pancreatic cancer, gastric cancer, esophageal cancer, renal cancer, hepatocellular carcinoma, sarcoma, germ cell tumors, leukemia, lymphoma, Hodgkin's lymphoma, skin cancer, Merkel cell carcinoma, testicular cancer and bladder cancer.

4. The method according to claim 1, wherein the patient has an advanced cancer, optionally with metastasis.

5. The method according to claim 4, wherein the advanced cancer is a stage III, stage IIIA, stage IIIB, stage IIIc, or stage IV cancer.

6. The method according to claim 1, wherein the peptide composition is administered every one to four weeks, every two to three weeks, or every three weeks.

7. The method according to claim 1, wherein the peptide composition is administered at least twice or at least three times.

8. The method according to claim 1, wherein the peptide composition is administered one week to three months after cancer progression or two weeks to two months after cancer progression.

9. The method according to claim 1, wherein the immune checkpoint inhibitor is a CTLA-4 inhibitor, a PD-1 inhibitor, a PD-L1 inhibitor or an indoleamine-pyrrole 2,3-dioxygenase (IDO) inhibitor.

10. The method according to claim 9, wherein the IDO inhibitor is indoximod.

11. The method according to claim 1, wherein the immune checkpoint inhibitor is selected from the group consisting of pembrolizumab, nivolumab, BMS936559, AMP-224, MEDI0680, avelumab, atezolizumab, durvalumab, tremelimumab and ipilimumab.

12. The method according to claim 1, wherein the immune checkpoint inhibitor is a PD-1 inhibitor.

13. A method of treating cancer in a Human Leukocyte Antigen A2 (HLA-A2) positive patient comprising administering, to a HLA-A2 positive patient having already been treated as a last treatment with a first immune checkpoint inhibitor alone or in combination with another cancer therapy and has cancer progression after the last treatment,
   a peptide composition comprising aKXVAAWTLKAAa (SEQ ID NO: 10, with X and a, respectively, indicating cyclohexylalanine and d-alanine) and at least 4, 5, 6, 7, 8 or 9 peptides selected from the group consisting of RLLQETELV (SEQ ID NO: 1), YLQLVFGIEV (SEQ ID NO: 2), LLTFWNPPV (SEQ ID NO: 3), KVFGSLAFV (SEQ ID NO: 4), KLBPVQLWV (SEQ ID NO: 5, with B indicating α-aminoisobutyric acid), SMPPPGTRV (SEQ ID NO: 6), IMIGHLVGV (SEQ ID NO: 7), KVAEIVHFL (SEQ ID NO: 8), and YLSGADLNL (SEQ ID NO: 9) and
   a second immune checkpoint inhibitor to the patient, wherein said patient has cancer progression after administration of the peptide composition.

14. A method of treating cancer in an HLA-A2 positive patient, wherein the patient received an immune checkpoint inhibitor as a last treatment, alone or in combination with another cancer therapy, the method comprising
   a) administering a therapeutically effective amount of a peptide composition comprising the peptide aKXVAAWTLKAAa (SEQ ID NO: 10, with X and a respectively indicating cyclohexylalanine and d-alanine) and at least 4, 5, 6, 7, 8 or 9 peptides selected from the group consisting of RLLQETELV (SEQ ID NO: 1), YLQLVFGIEV (SEQ ID NO: 2), LLTFWNPPV (SEQ ID NO: 3), KVFGSLAFV (SEQ ID NO: 4), KLBPVQLWV (SEQ ID NO: 5, with B indicating α-aminoisobutyric acid), SMPPPGTRV (SEQ ID NO: 6), IMIGHLVGV (SEQ ID NO: 7), KVAEIVHFL (SEQ ID NO: 8), and YLSGADLNL (SEQ ID NO: 9);
   b) administering a therapeutically effective amount of an immune checkpoint inhibitor when a cancer progression occurs with the treatment with the peptide composition; and
   c) optionally administering a therapeutically effective amount of a peptide composition as defined herein;
wherein steps a), b) and c) are sequential and wherein steps b) and c) can be repeated as long as the patient has a therapeutic benefit from the sequential treatment.

15. The method according to claim 14, wherein the immune checkpoint inhibitor is a CTLA-4 inhibitor, a PD-1 inhibitor, a PD-L1 inhibitor, an IDO inhibitor, or a combination thereof.

16. The method according to claim 15, wherein the IDO inhibitor is indoximod.

17. The method according to claim 14, wherein the immune checkpoint inhibitor is selected from the group consisting of pembrolizumab, nivolumab, BMS936559, AMP-224, MEDI0680, avelumab, atezolizumab, durvalumab, tremelimumab and ipilimumab.

* * * * *

UNITED STATES PATENT AND TRADEMARK OFFICE
CERTIFICATE OF CORRECTION

Page 1 of 1

PATENT NO. : 11,696,936 B2
APPLICATION NO. : 16/767144
DATED : July 11, 2023
INVENTOR(S) : Dominique Costantini It is certified that error appears in the above-identified patent and that said Letters Patent is hereby corrected as shown below:

In the Specification

Column 14,
Line 54, "by $2_{nd}$" should read --by $2^{nd}$--.

Signed and Sealed this
Second Day of January, 2024

Katherine Kelly Vidal
*Director of the United States Patent and Trademark Office*